US007468422B2

(12) United States Patent
Honore et al.

(10) Patent No.: US 7,468,422 B2
(45) Date of Patent: Dec. 23, 2008

(54) MECHANOSENSITIVE MAMMALIAN POTASSIUM CHANNEL ACTIVATABLE BY POLYUNSATURATED FATTY ACIDS

(75) Inventors: Eric Honore, Juan les Pins (FR); Michel Fink, Fresne (FR); Michel Lazdunski, Nice (FR); Florian Lesage, Nice (FR); Fabrice Duprat, Vallauris (FR)

(73) Assignee: Centre National de la Recherche Scientifique - CNRS (FR)

( * ) Notice: Subject to any disclaimer, the term of this patent is extended or adjusted under 35 U.S.C. 154(b) by 119 days.

(21) Appl. No.: 11/224,260

(22) Filed: Sep. 12, 2005

(65) Prior Publication Data

US 2006/0024729 A1 Feb. 2, 2006

Related U.S. Application Data

(60) Division of application No. 09/655,272, filed on Sep. 5, 2000, now Pat. No. 6,942,979, which is a continuation of application No. PCT/FR99/00404, filed on Feb. 23, 1999.

(30) Foreign Application Priority Data

Mar. 5, 1998 (FR) .................................. 98 02725

(51) Int. Cl.
*C07K 14/435* (2006.01)
*C07K 14/705* (2006.01)
*C07H 21/04* (2006.01)
*C12N 5/00* (2006.01)
*G01N 33/53* (2006.01)

(52) U.S. Cl. ..................................... 530/350; 536/23.1
(58) Field of Classification Search .................. None
See application file for complete search history.

(56) References Cited

FOREIGN PATENT DOCUMENTS

FR 2 744 730 A1 8/1997
WO WO 96/03415 A1 2/1996

OTHER PUBLICATIONS

Kim, D. Physiology and pharmacology of two-pore domain potassium channels. Curr Pharmaceut Design 11:2717-2736, 2005.*
Donghee Kim, A Mechanosensitive $K^+$ Channel in Heart Cells, *Journal of General Physiology*, vol. 100, No. 6, Dec. 1992, pp. 1021-1040.
Michel Fink et al., Clonging functional expression and brain localization of a novel unconventional outward rectifier $K^+$ channel, *The EMBO Journal*, vol. 15, No. 24, 1996, pp. 6854-6862.
Michael Fink et al., A neuronal two P domain $K^+$ channel stimulated by arachidonic acid and polyunsaturated fatty acids, *The EMBO Journal*, vol. 17, No. 12, 1998, pp. 3297-3308.
Amanda J. Patel et al., A mammalian two pore domain mechanogated S-like $K^+$ channel, *The EMBO Journal*, vol. 17, No. 15, 1998, pp. 4283-4290.
Francois Maingret et al., TRAAK is a Mammalian Neuronal Mechano-gated $K^+$ Channel, *The Journal of Biological Chemistry*, vol. 274, No. 3, Jan. 15, 1999, pp. 1381-1387.
Francois Maingret et al., *Lysophospholipids Open Two-pore Domain Mechano-gated $K^+$ Channels TREK-1 and TRAAK*, *The Journal of Biological Chemistry*, vol. 275, No. 14, Apr. 7, 2000, pp. 10128-10133.
Amanda J. Patel et al., Inhalational anesthetics activate two-pore-domain background $K^+$ channels, *Nature Neuroscience*, vol. 2, No. 5, May 1999, pp. 422-426.
Roberto Reyes et al., Cloning and Expression of a Novel pH-sensitive Two Pore Domain $K^+$ Channel from Human Kidney, *The Journal of Biolgical Chemistry*, vol. 273, No. 47, Nov. 20, 1998, pp. 30863-30869.
Rose A. Gubitosi-Klug et al., Concomitant Acceleration of the Activation and Inactivation Kinetics of the Human Delayed Rectifier $K^+$ Channel (Kv1.1) by $Ca^{2+}$-independent Phospholipase $A_2$, *The Journal of Biological Chemistry*, vol. 270, No. 7, Feb. 17, 1995, pp. 2885-2888.
Jeffrey Skolnick et al., From genes to protein structure and function: novel applications of computational approaches in the genomic era, *Trends in Biotech*, 18(1), 2000, pp. 34-39.
Peer Bork, Powers and Pitfalls in Sequence Analysis: The 70% Hurdle, *Genome Research*, 10, 2000, pp. 398-400.
Tobias Doerks et al., Protein annotation: detective work for function prediction, *Trends in Genetics*, vol. 14, No. 6, Jun. 1998, pp. 248-250.
Temple F. Smith et al., The challenges of genome sequence annotation or "The devil is in the details", *Nature Biotechnology*, vol. 15, Nov. 1997, pp. 1222-1223.
Steven E. Brenner, Errors in genome annotation, *Trends in Genetics*, 15(4), 1999, pp. 132-133.
Peer Bork et al., Go hunting in sequence databases but watch out for the traps, *Trends in Genetics*, vol. 12, No. 10, Oct. 1996, pp. 425-427.
James A. Wells, Additivity of Mutational Effects in Proteins, *Biochemistry*, vol. 29, No. 37, Sep. 18, 1990, pp. 8509-8517.
J. Thomas Ngo et al., Computational Complexity, Protein Structure Prediction and the Levinthal Paradox, *The Protein Folding Problem and Tertiary Structure Prediction*, 1994, pp. 492-495.
Frank Lehmann-Horn et al., Voltage-Gated ion Channels and Hereditary Disease, *Physiological Review*, vol. 79, No. 4, Oct. 1999, pp. 1317-1372.
Raymond A. Chavez et al., TWIK-2, a New Weak Inward Rectifying Member of the Tandem Pore Domain Potassium Channel Family, *The Journal of Biological Chemistry*, vol. 274, No. 12, Mar. 19, 1999, pp. 7887-7892.

* cited by examiner

*Primary Examiner*—Bridget E Bunner
(74) *Attorney, Agent, or Firm*—DLA Piper LLP (US)

(57) ABSTRACT

A purified protein including a mechanosensitive potassium channel activated by at least one polyunsaturated fatty acid and riluzole and the use of channels in drug screening.

7 Claims, 10 Drawing Sheets

Fig. 1

```
   1 ccacgcgtccgcggacgcgtgggtcgcccacgcgtccggtggcggctgtcc
  52 tgagccccgggccagctgatgtccaggttagggcagcgttggggccccaat
 103 cccagcctggaaggttggacttcacgtcgaccttctctgagtcttctgcc
 154 actcactggcctggacaagacagcattggggagcccagaggctgcaggtgc
 205 agtgaccactgctccccaggagctccctgctccttcttcccaggcaggaag
 256 tggagctggacctgcctctggaaggaccATGCGCAGCACCACACTCCTGGC
   1                               M  R  S  T  T  L  L  A 307 TCTGCTGGCACTGGTGCTGCTTTACTTGGTATCTGGGGCTCTAGTGTTCCA
   9  L  L  A  L  V  L  L  Y  L  V  S  G  A  L  V  F  Q 358 GGCTCTGGAGCAGCCTCACGAGCAGCAGGCTCAGAAGAAAATGGATCATGG
  26  A  L  E  Q  P  H  E  Q  Q  A  Q  K  K  M  D  H  G 409 CCGAGACCAGTTTCTGAGGGACCATCCCTGTGTGAGCCAGAAGAGCCTGGA
  43  R  D  Q  F  L  R  D  H  P  C  V  S  Q  K  S  L  E 460 GGATTTCATCAAGCTCCTGGTTGAAGCCCTGGGAGGGGGCGCAAACCCAGA
  60  D  F  I  K  L  L  V  E  A  L  G  G  A  N  P  E 511 AACCAGCTGGACCAATAGCAGCAACCACTCATCAGCTTGGAACCTGGGCAG
  77  T  S  W  T  N  S  S  N  H  S  S  A  W  N  L  G  S 562 CGCCTTCTTTTTCTCGGGGACCATCATCACTACCATCGGCTATGGCAATAT
  94  A  F  F  F  S  G  T  I  I  T  T  I  G  Y  G  N  I 613 AGTCTTACACACAGATGCCGGGCGTCTCTTTTGTATCTTCTATGCACTGGT
 111  V  L  H  T  D  A  G  R  L  F  C  I  F  Y  A  L  V 664 GGGGATCCCACTGTTCGGGATGCTGCTGGCGGGAGTCGGGGACCGGCTGGG
 128  G  I  P  L  F  G  M  L  L  A  G  V  G  D  R  L  G 715 CTCCTCTCTGCGCCGGGGCATCGGCCACATCGAAGCAATCTTCTTGAAGTG
 145  S  S  L  R  R  G  I  G  H  I  E  A  I  F  L  K  W 766 GCATGTGCCACCGGGGCTGGTGAGAAGTCTGTCCGCAGTGCTCTTCCTGCT
 162  H  V  P  P  G  L  V  R  S  L  S  A  V  L  F  L  L 817 GATCGGCTGCCTGCTCTTTGTCCTCACTCCTACCTTCGTGTTCTCCTACAT
 179  I  G  C  L  L  F  V  L  T  P  T  F  V  F  S  Y  M 868 GGAGAGCTGGAGCAAGTTAGAAGCCATCTACTTTGTTATAGTGACTCTCAC
 196  E  S  W  S  K  L  E  A  I  Y  F  V  I  V  T  L  T 919 CACTGTAGGCTTTGGCGATTATGTACCCGGCGATGGCACCGGGCAGAACTC
 213  T  V  G  F  G  D  Y  V  P  G  D  G  T  G  Q  N  S 970 TCCAGCCTACCAGCCGCTGGTGTGGTTCTGGATCTTGTTTGGCCTAGCCTA
 230  P  A  Y  Q  P  L  V  W  F  W  I  L  F  G  L  A  Y 1021 CTTCGCCTCAGTGCTCACCACCATCGGCAACTGGTTGCGAGCAGTGTCCCG
 247  F  A  S  V  L  T  T  I  G  N  W  L  R  A  V  S  R 1072 CCGAACTCGGGCAGAGATGGGTGGCCTAACGGCACAGGCTGCTAGCTGGAC
 264  R  T  R  A  E  M  G  G  L  T  A  Q  A  A  S  W  T 1123 CGGCACAGTGACAGCGCGAGTGACCCAGCGAACTGGGCCCAGCGCCCCGCC
 281  G  T  V  T  A  R  V  T  Q  R  T  G  P  S  A  P  P 1174 GCCAGAGAAGGAGCAACCACTCCTGCCCCTCCTCTTTGCCGGCACCGCCTGC
 298  P  E  K  E  Q  P  L  L  P  S  S  L  P  A  P  P  A 1225 TGTTGTTGAGCCAGCCGGCAGGCCCGGCTCCCCTGCACCCGCAGAGAAGGT
 315  V  V  E  P  A  G  R  P  G  S  P  A  P  A  E  K  V 1276 TGAGACTCCGTCCCCGCCCACGGCCTCAGCTCTGGATTACCCCAGTGAGAA
 332  E  T  P  S  P  P  T  A  S  A  L  D  Y  P  S  E  N 1327 TCTGGCCTTCATCGACGAGTCCTCAGACACGCAGAGTGAGCGTGGCTGTGC
 349  L  A  F  I  D  E  S  S  D  T  Q  S  E  R  G  C  A 1378 CCTGCCCTCGGGCTCCTCGGGGTCGCCGCCGACCCAACCCATCCAAAAAGCC
 366  L  P  R  A  P  R  G  R  R  R  P  N  P  S  K  K  P 1429 TTCCAGACCCCGGGGTCCTGGGCGACTCCGAGACAAGGCCGTGCCGGTGTA
 383  S  R  P  R  G  P  G  R  L  R  D  K  A  V  P  V  *

1480 Ggggcaggatctctggacccggatcccacgccagggctttcgctcttgctg
 399

1531 atgctcaggcatgcttggcttatttgaccaaagagccgtccctctttgtt
1582 ccacgtggttgcaaccctgacaggagtccagtggttgccaaatgccaccgc
1633 tcttccctggctggttcttcacatccaatcatttccaaagcccaccatcca
1684 aggctttctgcctcgctcccctgccggttttgaccctcacacctcacaact
1735 gtgcctcaaaacctgcaccaata
```

Fig.2

```
TWIK    1   ........................MLQSLAGSSCVRLV
TREK    1   MAAPDLLDPKSAAQNSKPRLSFSSKPTVLASRVESDSA
TASK    1   ......................................
TRAAK   1   ......................................

M1
TWIK   15   ERHRSAWCFGFLVLGYLLYLVFGAVVFSSVELPYEDLL
TREK   39   INVMKWKIVSTIFLVVLYLIIGAAVFKALEQPQEISQ
TASK    1   -MKRQNVRTLALIVCTFTYLLVGAAVFDALESEPELIE
TRAAK   1   ---MRSTLLALLAFVLLVSGALVFQALEQPHEQQA

TWIK   53   RQELRKLKRRFLEEHECLSEQQLEQFLGRVLEASNYGV
TREK   77   RTTIVIQKQTFIAQHACVNSTELDELIQQIVAAINAGI
TASK   38   RQRLELR-QQELRARYNLSQGGYEELERVVLR---LKP
TRAAK  36   QKKMDHGRDQFLRDHPCVSQKSLEDFIKLLVEALGGGA

P1
TWIK   91   SVLS---NASG-NWNWDFTSALFFASTVLSTTGYGHTV
TREK  115   IPLG---NSSNQVSHWDLGSSFFAGTVITTIGFGNIS
TASK   72   HKAG--------VQWRFAGSFYFAITVITTIGYGHAA
TRAAK  74   NPETSWTNSSMHSSAWNLGSAFFFSGTIITTIGYGNIV

M2
TWIK  125   PLSDGGKAFCTIVSVIGIPFTLFLTAVVQRITVHVTR
TREK  150   PRTEGGKIFCLIYALLGIPLFLLAGVGDQLGTIIFGK
TASK  101   PSTDGGKVFCMFYALLGIPLTLVMFQSLGERINTLVRY
TRAAK 112   LHTDAGRLFCIFYALVGIPIFGMLLAGVGDRLGSSLRR

M3
TWIK  163   ---RPVLYFHIRWGFSKQVVAIVHAVLIGFVTVSCFFI
TREK  188   GIAKVEDTFIKWNVSQTKTRIIST-LLFILFGCVLFVAL
TASK  139   ---LLHRAKKGLGMRRADVSMANMVLIGFFSCISTLCI
TRAAK 150   GIGHIEAIFLKWHVPPGLVRSLSAVLFLLIGCLLFVLT

P2
TWIK  199   PAAVFSVLEDDWNFLESFYFCFISLSTIGLGDYVPG-E
TREK  226   PAVIFKHIEG-WSALDAIYFVVITLSTIGFGDYVAG-G
TASK  174   GAAAFSHYEH-WTFFQAYYYCFITLTTIGFGDYVALQK
TRAAK 188   PTFVFSYMES-WSKLEAIYFVIVTLTTVGFGDYVPG-D

M4
TWIK  236   GYNQKFRELYKIGITCYLLGFTAMLVVLETFCELHEL
TREK  262   SDIEYL-DFYKPVVWFWILVGLAYFAAVLSMIGDWLRV
TASK  211   DQALQTQPQYVAFSFVYILTGLTVIGAFLNLVVLRFMT
TRAAK 224   GTGQNS-PAYQPLVWFWILFGLAYFASVLTTIGNWLRA

TWIK  274   KKFRKMFYVKKDKDEDQ..............VHFIEHD-
TREK  299   ISKKTKEEVGEFRAHAAE......WTANVTAEFKETR-
TASK  249   MNAEDEKRDAEHRALLTRNGQAGGGGGGSAHTTDTAS
TRAAK 261   VSRRTRAEMGGLTAQAAS-----WTGTVTARVTQRTG

TWIK  298   ..........................QLS
TREK  330   ..........................RRL
TASK  287   STAAAGGGGFRNVYAEVLHFQSMCSCLWYKSREKLQYS
TRAAK 293   PSAPPPE------KEQPLLPSSLPAPPAVVEPAGRPG

TWIK  301   FSSITDQAAG----MK---E-DQKQNEPEVATQS-SAGV
TREK  333   SVELYDKFQR---ATSVKRKLSAELAGNHNQELTPCM
TASK  325   IPMIIPRDLS----TSDICVEQSHSSPGGGRYSDTPS
TRAAK 324   SPAPAEKVETPSPPTASLDYPSENLAFIDESSDTQSE

TWIK  331   DGPANH.......................
TREK  367   RTCL.........................
TASK  359   RRCLCSGAPRSAISSVSTGLHSLSTFRGLMKRRSSV-
TRAAK 362   RGCALPRAPRGRRGPNPSKKPSRPGPGRLRDKAVPV
```

```
                              TREK
                              TRAAK
                              TWIK
                              TASK
```

Fig.4
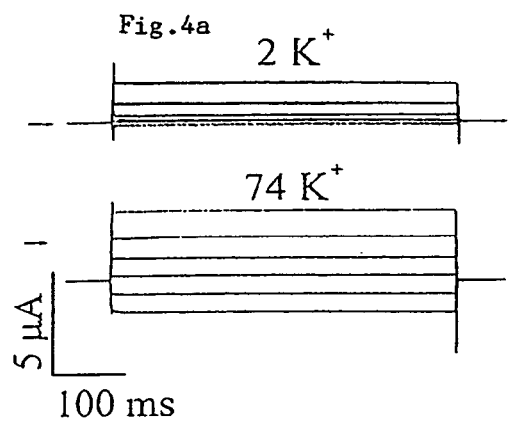
Fig.4a
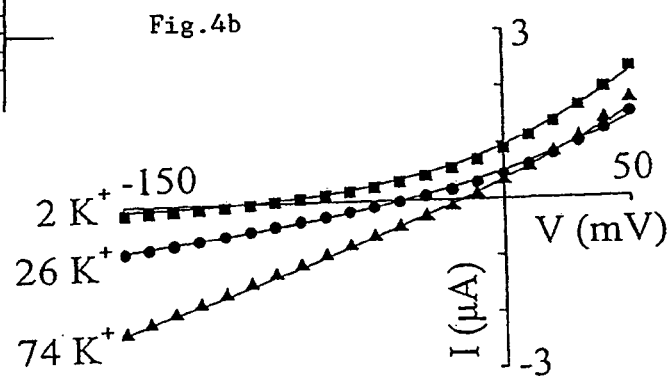
Fig.4b
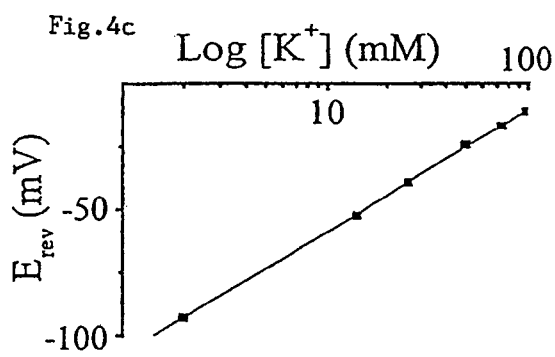
Fig.4c
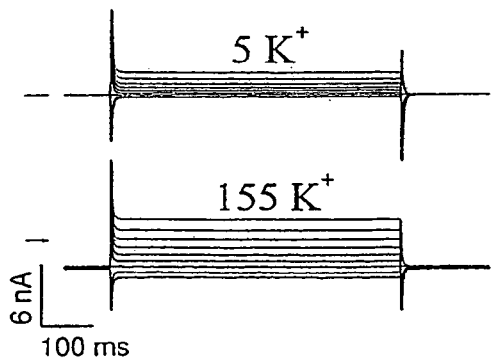
Fig.4d
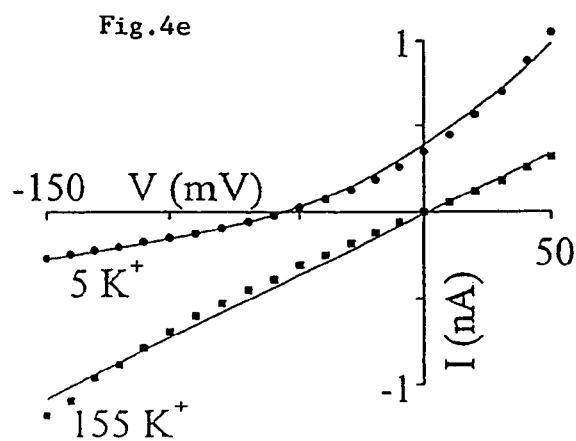
Fig.4e Fig.5
Fig.5a
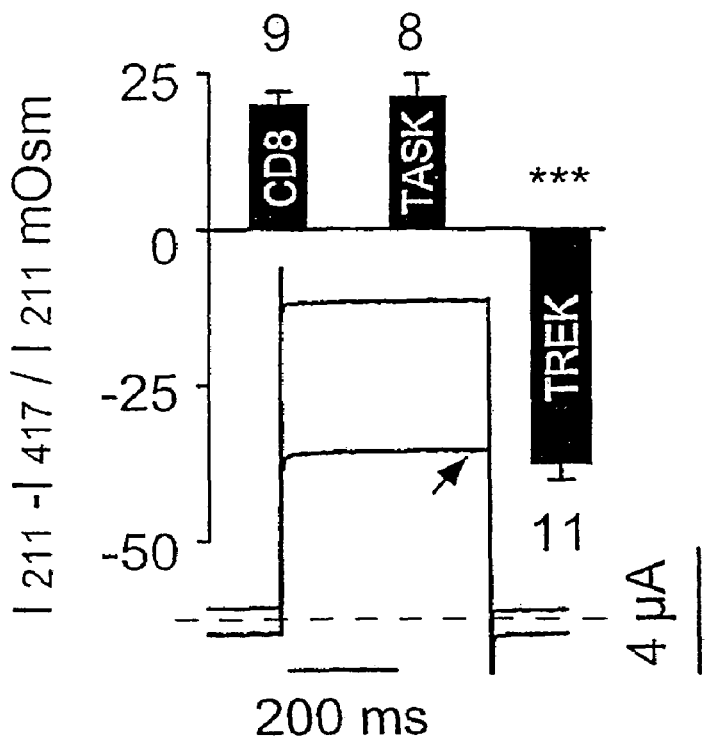
Fig.5b
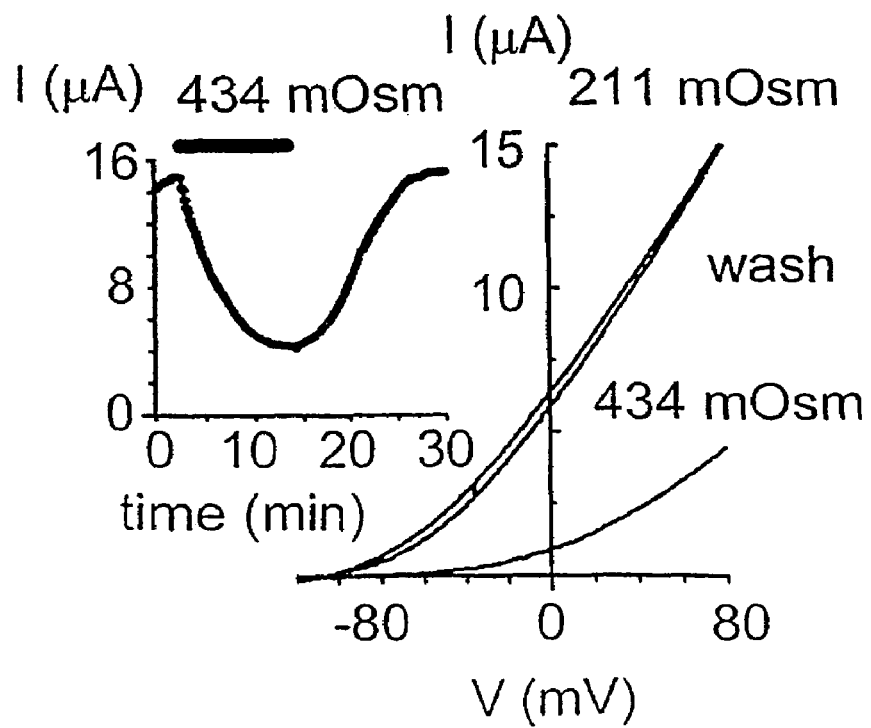

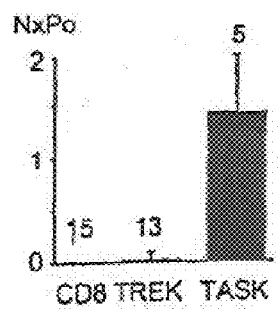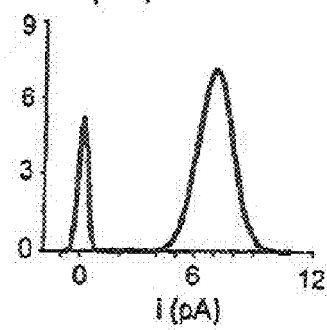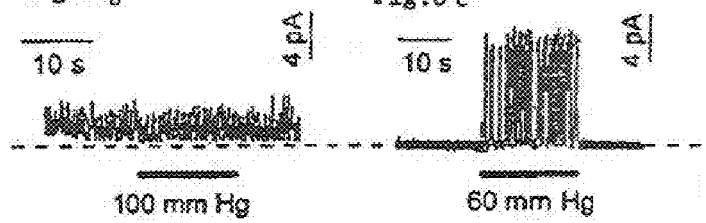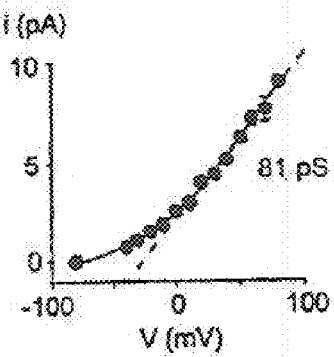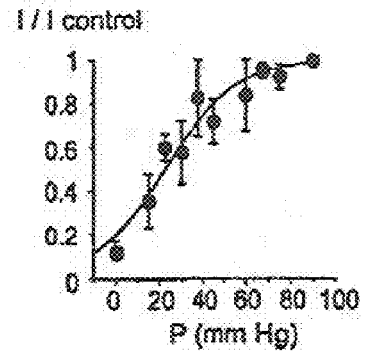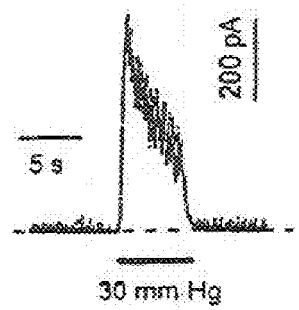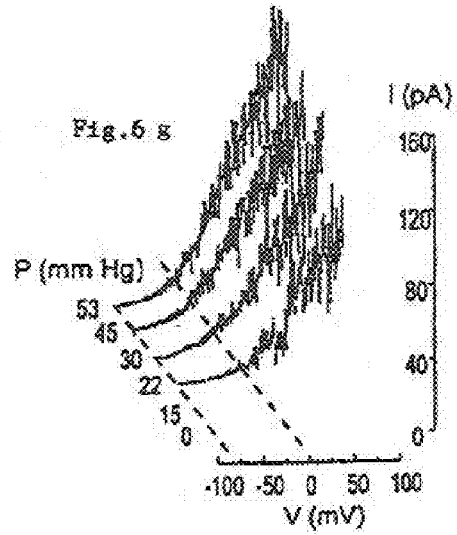
Fig. 6

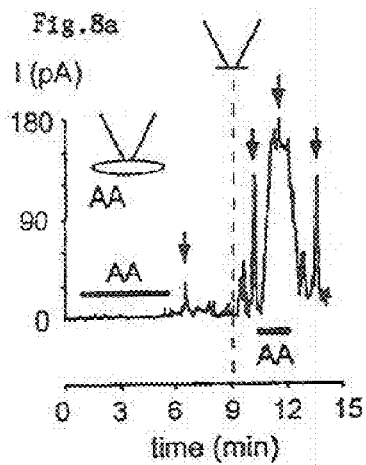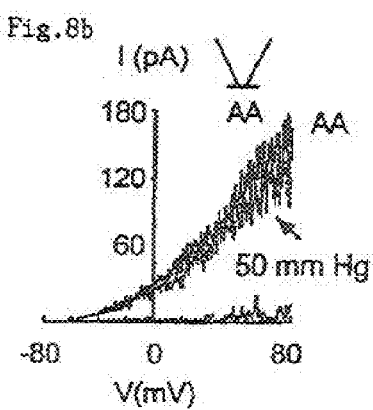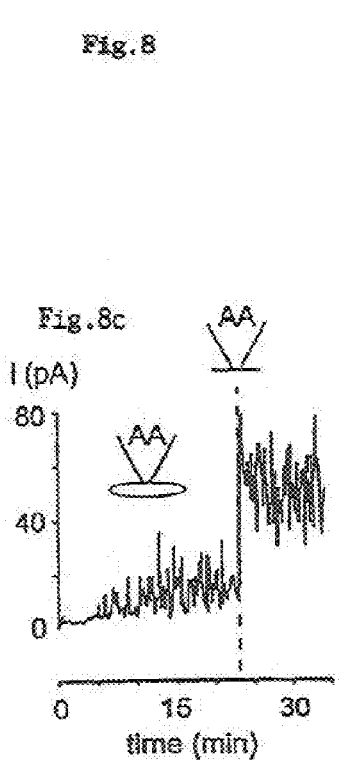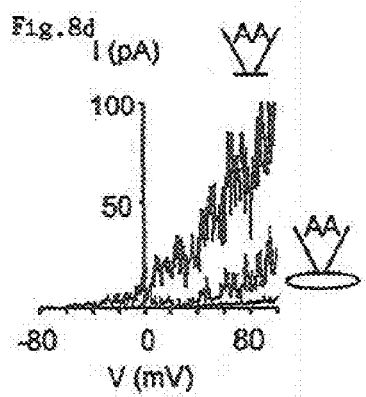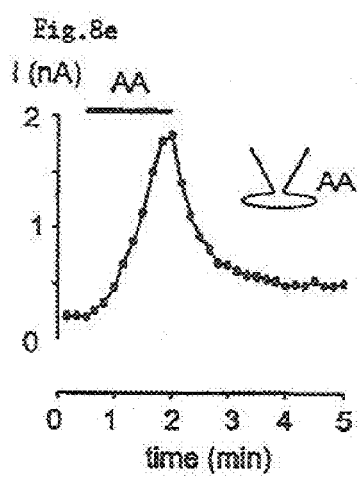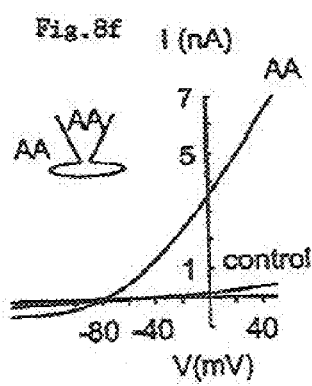

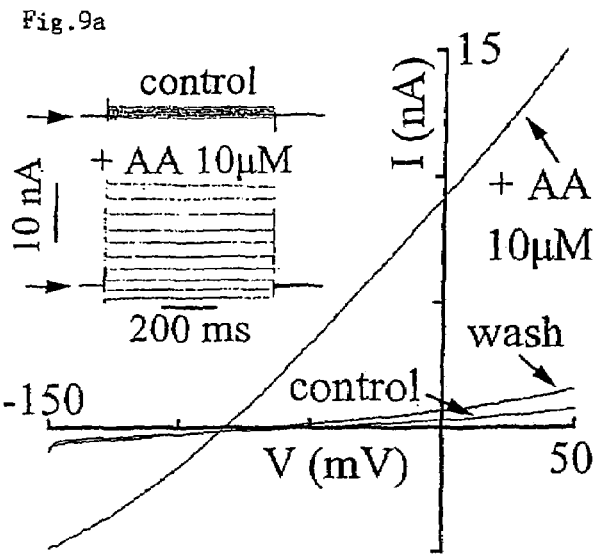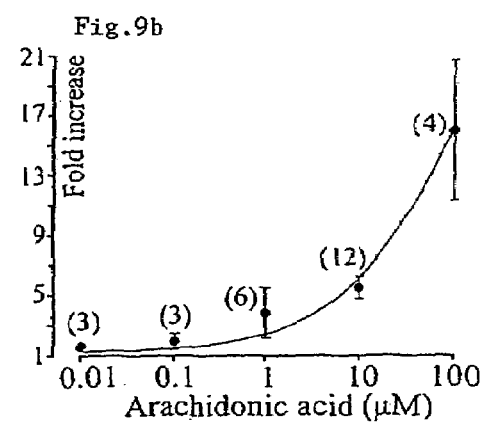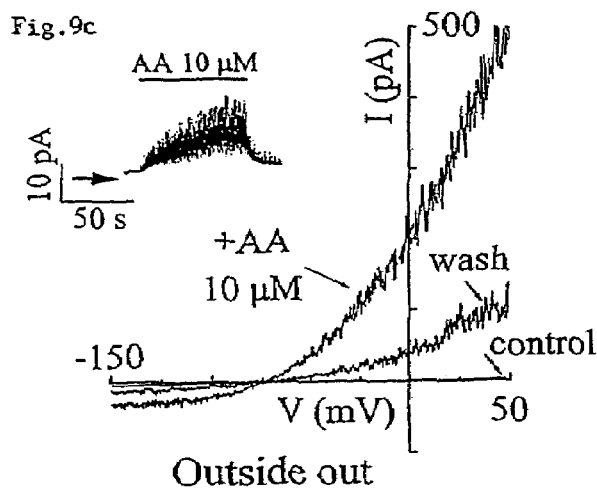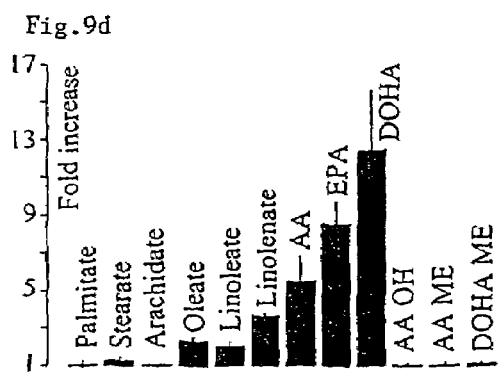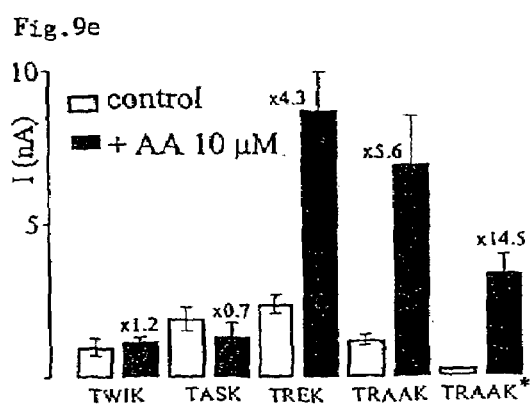

Fig. 10
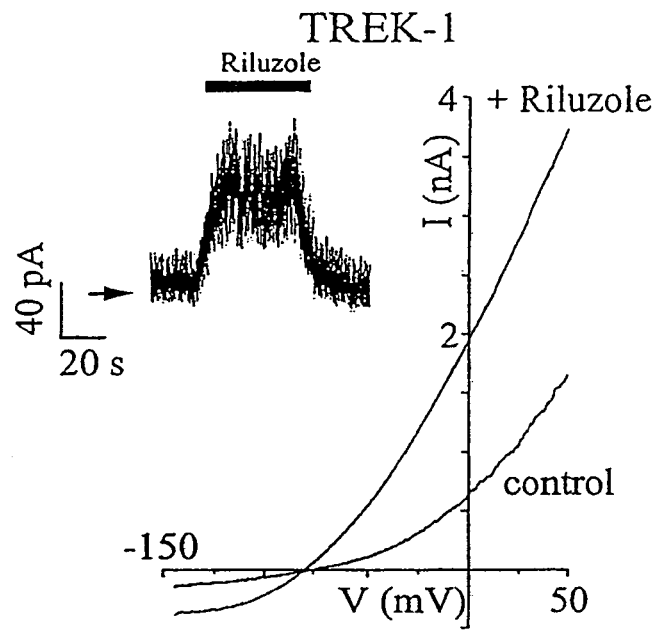
Fig. 10a
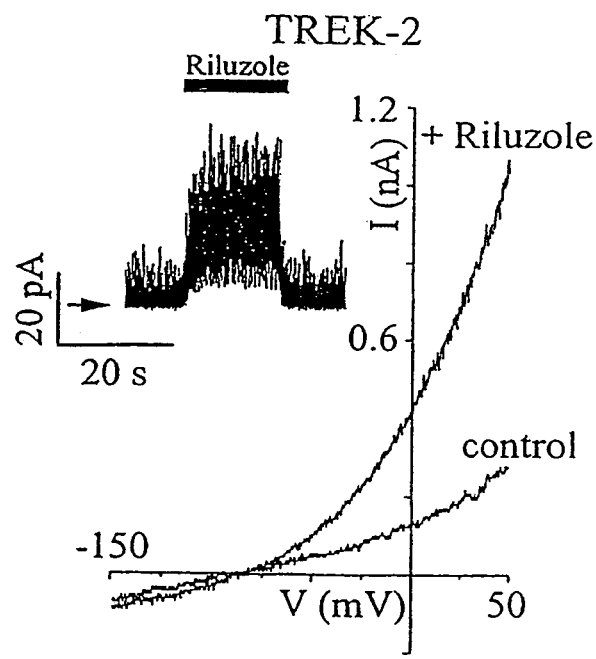
Fig. 10b

SEQUENCE LISTING

```
<160> NUMBER OF SEQ ID NOS: 6

<210> SEQ ID NO 1
<211> LENGTH: 1757
<212> TYPE: DNA
<213> ORGANISM: Unknown Sequence
<220> FEATURE:
<223> OTHER INFORMATION: Description of Unknown Sequence: DNA encoding
      TRAAK
```

```
<220> FEATURE:
<221> NAME/KEY: CDS
<222> LOCATION: (284)..(1477)

<400> SEQUENCE: 1
ccacgcgtcc gcggacgcgt gggtcgccca cgcgtccggt ggcggctgtc ctgagccccg      60
ggccagctga tgtccaggtt agggcagcgt tggggcccca atcccagcct ggaaggttgg     120
acttcacgtc gaccctttctc tgagtcttct gccactcact ggcctggaca agacagcatt    180
ggggagccca gaggctgcag gtgcagtgac cactgctccc caggagctcc ctgctccttc     240
ttcccaggca ggaagtggag ctggacctgc tctggaagg acc atg cgc agc acc       295
                                              Met Arg Ser Thr
                                                1 aca ctc ctg gct ctg ctg gca ctg gtg ctg ctt tac ttg gta tct ggg       343
Thr Leu Leu Ala Leu Leu Ala Leu Val Leu Leu Tyr Leu Val Ser Gly
  5                  10                  15                  20 gct cta gtg ttc cag gct ctg gag cag cct cac gag cag cag gct cag       391
Ala Leu Val Phe Gln Ala Leu Glu Gln Pro His Glu Gln Gln Ala Gln
             25                  30                  35 aag aaa atg gat cat ggc cga gac cag ttt ctg agg gac cat ccc tgt       439
Lys Lys Met Asp His Gly Arg Asp Gln Phe Leu Arg Asp His Pro Cys
         40                  45                  50 gtg agc cag aag agc ctg gag gat ttc atc aag ctc ctg gtt gaa gcc       487
Val Ser Gln Lys Ser Leu Glu Asp Phe Ile Lys Leu Leu Val Glu Ala
     55                  60                  65 ctg gga ggg ggc gca aac cca gaa acc agc tgg acc aat agc agc aac       535
Leu Gly Gly Gly Ala Asn Pro Glu Thr Ser Trp Thr Asn Ser Ser Asn
 70                  75                  80 cac tca tca gct tgg aac ctg ggc agc gcc ttc ttt tcg ggg acc          583
His Ser Ser Ala Trp Asn Leu Gly Ser Ala Phe Phe Phe Ser Gly Thr
 85                  90                  95                 100 atc atc act acc atc ggc tat ggc aat ata gtc tta cac aca gat gcc       631
Ile Ile Thr Thr Ile Gly Tyr Gly Asn Ile Val Leu His Thr Asp Ala
                105                 110                 115 ggg cgt ctc ttt tgt atc ttc tat gca ctg gtg ggg atc cca ctg ttc       679
Gly Arg Leu Phe Cys Ile Phe Tyr Ala Leu Val Gly Ile Pro Leu Phe
            120                 125                 130 ggg atg ctg ctg gcg gga gtc ggg gac cgg ctg ggc tcc tct ctg cgc       727
Gly Met Leu Leu Ala Gly Val Gly Asp Arg Leu Gly Ser Ser Leu Arg
        135                 140                 145 cgg ggc atc ggc cac atc gaa gca atc ttc ttg aag tgg cat gtg cca       775
Arg Gly Ile Gly His Ile Glu Ala Ile Phe Leu Lys Trp His Val Pro
    150                 155                 160 ccg ggg ctg gtg aga agt ctg tcc gca gtg ctc ttc ctg ctg atc ggc       823
Pro Gly Leu Val Arg Ser Leu Ser Ala Val Leu Phe Leu Leu Ile Gly
165                 170                 175                 180 tgc ctg ctc ttt gtc ctc act cct acc ttc gtg ttc tcc tac atg gag       871
Cys Leu Leu Phe Val Leu Thr Pro Thr Phe Val Phe Ser Tyr Met Glu
                185                 190                 195 agc tgg agc aag tta gaa gcc atc tac ttt gtt ata gtg act ctc acc       919
Ser Trp Ser Lys Leu Glu Ala Ile Tyr Phe Val Ile Val Thr Leu Thr
            200                 205                 210 act gta ggc ttt ggc gat tat gta ccc ggc gat ggc acc ggg cag aac       967
Thr Val Gly Phe Gly Asp Tyr Val Pro Gly Asp Gly Thr Gly Gln Asn
        215                 220                 225 tct cca gcc tac cag ccg ctg gtg tgg ttc tgg atc ttg ttt ggc cta      1015
Ser Pro Ala Tyr Gln Pro Leu Val Trp Phe Trp Ile Leu Phe Gly Leu
    230                 235                 240
```

-continued

```
gcc tac ttc gcc tca gtg ctc acc acc atc ggc aac tgg ttg cga gca      1063
Ala Tyr Phe Ala Ser Val Leu Thr Thr Ile Gly Asn Trp Leu Arg Ala
245                 250                 255                 260 gtg tcc cgc cga act cgg gca gag atg ggt ggc cta acg gca cag gct      1111
Val Ser Arg Arg Thr Arg Ala Glu Met Gly Gly Leu Thr Ala Gln Ala
                265                 270                 275 gct agc tgg acc ggc aca gtg aca gcg cga gtg acc cag cga act ggg      1159
Ala Ser Trp Thr Gly Thr Val Thr Ala Arg Val Thr Gln Arg Thr Gly
            280                 285                 290 ccc agc gcc ccg ccg cca gag aag gag caa cca ctc ctg ccc tcc tct      1207
Pro Ser Ala Pro Pro Pro Glu Lys Glu Gln Pro Leu Leu Pro Ser Ser
        295                 300                 305 ttg ccg gca ccg cct gct gtt gtt gag cca gcc ggc agg ccc ggc tcc      1255
Leu Pro Ala Pro Pro Ala Val Val Glu Pro Ala Gly Arg Pro Gly Ser
    310                 315                 320 cct gca ccc gca gag aag gtt gag act ccg tcc ccg ccc acg gcc tca      1303
Pro Ala Pro Ala Glu Lys Val Glu Thr Pro Ser Pro Pro Thr Ala Ser
325                 330                 335                 340 gct ctg gat tac ccc agt gag aat ctg gcc ttc atc gac gag tcc tca      1351
Ala Leu Asp Tyr Pro Ser Glu Asn Leu Ala Phe Ile Asp Glu Ser Ser
                345                 350                 355 gac acg cag agt gag cgt ggc tgt gcc ctg cct cgg gct cct cgg ggt      1399
Asp Thr Gln Ser Glu Arg Gly Cys Ala Leu Pro Arg Ala Pro Arg Gly
                360                 365                 370 cgc cgc cga ccc aac cca tcc aaa aag cct tcc aga ccc cgg ggt cct      1447
Arg Arg Arg Pro Asn Pro Ser Lys Lys Pro Ser Arg Pro Arg Gly Pro
            375                 380                 385 ggg cga ctc cga gac aag gcc gtg ccg gtg tagggggcagg atctctggac       1497
Gly Arg Leu Arg Asp Lys Ala Val Pro Val
        390                 395 ccggatccca cgccagggct ttcgctcttg ctgatgctca ggcatgcttg gcttatttga    1557
ccaaagagcc gtccctcttt tgttccacgt ggttgcaacc ctgacaggag tccagtggtt    1617
gccaaatgcc accgctcttc cctggctggt tcttcacatc caatcatttc caaagcccac    1677
catccaaggc tttctgcctc gctcccctgc cggttttgac cctcacacct cacaactgtg    1737
cctcaaaacc tgcaccaata                                                 1757

<210> SEQ ID NO 2
<211> LENGTH: 398
<212> TYPE: PRT
<213> ORGANISM: Unknown Sequence
<220> FEATURE:
<223> OTHER INFORMATION: Description of Unknown Sequence: TRAAK

<400> SEQUENCE: 2

Met Arg Ser Thr Thr Leu Leu Ala Leu Leu Ala Leu Val Leu Leu Tyr
1               5                   10                  15

Leu Val Ser Gly Ala Leu Val Phe Gln Ala Leu Glu Gln Pro His Glu
            20                  25                  30

Gln Gln Ala Gln Lys Lys Met Asp His Gly Arg Asp Gln Phe Leu Arg
        35                  40                  45

Asp His Pro Cys Val Ser Gln Lys Ser Leu Glu Asp Phe Ile Lys Leu
    50                  55                  60

Leu Val Glu Ala Leu Gly Gly Gly Ala Asn Pro Glu Thr Ser Trp Thr
65                  70                  75                  80

Asn Ser Ser Asn His Ser Ser Ala Trp Asn Leu Gly Ser Ala Phe Phe
                85                  90                  95
```

```
Phe Ser Gly Thr Ile Ile Thr Thr Ile Gly Tyr Gly Asn Ile Val Leu
                100                 105                 110
His Thr Asp Ala Gly Arg Leu Phe Cys Ile Phe Tyr Ala Leu Val Gly
            115                 120                 125
Ile Pro Leu Phe Gly Met Leu Ala Gly Val Gly Asp Arg Leu Gly
        130                 135                 140
Ser Ser Leu Arg Arg Gly Ile Gly His Ile Glu Ala Ile Phe Leu Lys
145                 150                 155                 160
Trp His Val Pro Pro Gly Leu Val Arg Ser Leu Ser Ala Val Leu Phe
                165                 170                 175
Leu Leu Ile Gly Cys Leu Leu Phe Val Leu Thr Pro Thr Phe Val Phe
            180                 185                 190
Ser Tyr Met Glu Ser Trp Ser Lys Leu Glu Ala Ile Tyr Phe Val Ile
        195                 200                 205
Val Thr Leu Thr Thr Val Gly Phe Gly Asp Tyr Val Pro Gly Asp Gly
    210                 215                 220
Thr Gly Gln Asn Ser Pro Ala Tyr Gln Pro Leu Val Trp Phe Trp Ile
225                 230                 235                 240
Leu Phe Gly Leu Ala Tyr Phe Ala Ser Val Leu Thr Thr Ile Gly Asn
                245                 250                 255
Trp Leu Arg Ala Val Ser Arg Arg Thr Arg Ala Glu Met Gly Gly Leu
            260                 265                 270
Thr Ala Gln Ala Ala Ser Trp Thr Gly Thr Val Thr Ala Arg Val Thr
        275                 280                 285
Gln Arg Thr Gly Pro Ser Ala Pro Pro Glu Lys Glu Gln Pro Leu
    290                 295                 300
Leu Pro Ser Ser Leu Pro Ala Pro Ala Val Val Glu Pro Ala Gly
305                 310                 315                 320
Arg Pro Gly Ser Pro Ala Pro Ala Glu Lys Val Glu Thr Pro Ser Pro
                325                 330                 335
Pro Thr Ala Ser Ala Leu Asp Tyr Pro Ser Glu Asn Leu Ala Phe Ile
            340                 345                 350
Asp Glu Ser Ser Asp Thr Gln Ser Glu Arg Gly Cys Ala Leu Pro Arg
        355                 360                 365
Ala Pro Arg Gly Arg Arg Pro Asn Pro Ser Lys Lys Pro Ser Arg
    370                 375                 380
Pro Arg Gly Pro Gly Arg Leu Arg Asp Lys Ala Val Pro Val
385                 390                 395
```

<210> SEQ ID NO 3
<211> LENGTH: 1993
<212> TYPE: DNA
<213> ORGANISM: Unknown Organism
<220> FEATURE:
<223> OTHER INFORMATION: Description of Unknown Organism: DNA encoding TREK
<220> FEATURE:
<221> NAME/KEY: CDS
<222> LOCATION: (484)..(1593)

<400> SEQUENCE: 3
agagcggcga ggcgagggga gagtggtgct acgggccagg cgggccaccc cgggccacac    60
ccccaccttg cgggcgcccg gcggggctcg agccaggcgg ggcgcctcac aaagacatgc   120
gaagaggggc tgcagtgatc accccctcgc tgaccccgg gcagagccc agccgccggc    180 cgagcgcacg gagccacggg ccgagcgcac ccagggcccg cgcgggaccc caggcggcca   240

```
                                                  -continued cgcaatcggg gtgacccatc gcgcgcgggg gcgtcgtcgt ccgatcccaa cttggcctcg      300
gcctcgccct ctgcccagcc tgccaccgct ggtgtcctct ccttccggcg atttcgtttc      360
ttctcacgct cccccctcta tacccctccc gcctccagcc ccgctctccc caccttgtaa      420
aacaaagccg gggaaaatgc ctacccgtgc agctcggagc gcgcagcccg tcttggaata      480 agg atg gcg gcc cct gac ttg ctg gat ccc aag tct gct gct cag aac         528
    Met Ala Ala Pro Asp Leu Leu Asp Pro Lys Ser Ala Ala Gln Asn
    1               5                   10                  15 tcc aaa ccg agg ctc tca ttc tct tca aaa ccc acc gtg ctt gct tcc         576
Ser Lys Pro Arg Leu Ser Phe Ser Ser Lys Pro Thr Val Leu Ala Ser
                20                  25                  30 cgg gtg gag agt gac tcg gcc att aat gtt atg aaa tgg aag aca gtc         624
Arg Val Glu Ser Asp Ser Ala Ile Asn Val Met Lys Trp Lys Thr Val
            35                  40                  45 tcc acg att ttc ctg gtg gtc gtc ctc tac ctg atc atc gga gcc gcg         672
Ser Thr Ile Phe Leu Val Val Val Leu Tyr Leu Ile Ile Gly Ala Ala
        50                  55                  60 gtg ttc aag gca ttg gag cag cct cag gag att tcc cag agg acc acc         720
Val Phe Lys Ala Leu Glu Gln Pro Gln Glu Ile Ser Gln Arg Thr Thr
    65                  70                  75 att gtg atc cag aag cag acc ttc ata gcc cag cat gcc tgc gtc aac         768
Ile Val Ile Gln Lys Gln Thr Phe Ile Ala Gln His Ala Cys Val Asn
80                  85                  90                  95 tcc acc gag ctg gac gaa ctc atc cag caa ata gtg gca gca ata aac         816
Ser Thr Glu Leu Asp Glu Leu Ile Gln Gln Ile Val Ala Ala Ile Asn
                100                 105                 110 gca ggg att atc ccc tta gga aac agc tcc aat caa gtt agt cac tgg         864
Ala Gly Ile Ile Pro Leu Gly Asn Ser Ser Asn Gln Val Ser His Trp
            115                 120                 125 gac ctc gga agc tct ttc ttc ttt gct ggt act gtt atc aca acc ata         912
Asp Leu Gly Ser Ser Phe Phe Phe Ala Gly Thr Val Ile Thr Thr Ile
        130                 135                 140 gga ttt gga aac atc tcc cca cga act gaa ggt gga aaa ata ttc tgc         960
Gly Phe Gly Asn Ile Ser Pro Arg Thr Glu Gly Gly Lys Ile Phe Cys
    145                 150                 155 atc atc tat gcc ttg ctg gga att ccc ctc ttt ggc ttt cta ctg gct        1008
Ile Ile Tyr Ala Leu Leu Gly Ile Pro Leu Phe Gly Phe Leu Leu Ala
160                 165                 170                 175 ggg gtt ggt gat cag cta gga act ata ttt gga aaa gga att gcc aaa        1056
Gly Val Gly Asp Gln Leu Gly Thr Ile Phe Gly Lys Gly Ile Ala Lys
                180                 185                 190 gtg gaa gac aca ttt att aag tgg aat gtt agt cag acg aag att cgt        1104
Val Glu Asp Thr Phe Ile Lys Trp Asn Val Ser Gln Thr Lys Ile Arg
            195                 200                 205 atc atc tcc acc atc atc ttc atc ctg ttt ggc tgt gtc ctc ttt gtg        1152
Ile Ile Ser Thr Ile Ile Phe Ile Leu Phe Gly Cys Val Leu Phe Val
        210                 215                 220 gct ctc cct gcg gtc ata ttc aag cac ata gaa ggc tgg agc gcc ctg        1200
Ala Leu Pro Ala Val Ile Phe Lys His Ile Glu Gly Trp Ser Ala Leu
    225                 230                 235 gac gct atc tat ttt gtg gtt atc act ctg acg acc att gga ttt gga        1248
Asp Ala Ile Tyr Phe Val Val Ile Thr Leu Thr Thr Ile Gly Phe Gly
240                 245                 250                 255 gac tac gtg gca ggt gga tca gac att gaa tat ctg gac ttc tac aag        1296
Asp Tyr Val Ala Gly Gly Ser Asp Ile Glu Tyr Leu Asp Phe Tyr Lys
                260                 265                 270 cct gtg gtg tgg ttc tgg atc ctc gtt ggg ctg gcc tac ttt gca gct        1344
Pro Val Val Trp Phe Trp Ile Leu Val Gly Leu Ala Tyr Phe Ala Ala
            275                 280                 285
```

-continued

```
gtt ctg agc atg att ggg gac tgg cta cgg gtg atc tct aag aag acg      1392
Val Leu Ser Met Ile Gly Asp Trp Leu Arg Val Ile Ser Lys Lys Thr
        290                 295                 300 aag gaa gag gtg gga gag ttc aga gcg cat gcc gct gag tgg aca gcc      1440
Lys Glu Glu Val Gly Glu Phe Arg Ala His Ala Ala Glu Trp Thr Ala
305                 310                 315 aat gtc acg gcc gag ttc aag gaa acg agg agg cgg ctg agc gtg gag      1488
Asn Val Thr Ala Glu Phe Lys Glu Thr Arg Arg Arg Leu Ser Val Glu
320                 325                 330                 335 atc tac gac aag ttc cag cgt gcc aca tcc gtg aag cgg aag ctc tcc      1536
Ile Tyr Asp Lys Phe Gln Arg Ala Thr Ser Val Lys Arg Lys Leu Ser
                340                 345                 350 gca gag ctg gcg ggc aac cac aac cag gaa ctg act ccg tgt atg agg      1584
Ala Glu Leu Ala Gly Asn His Asn Gln Glu Leu Thr Pro Cys Met Arg
            355                 360                 365 acc tgt ctg tgaaccacct gaccagcgag agggaagtcc tgcctcccct            1633
Thr Cys Leu
        370 gctgaaggct gagagcatct atctgaacgg tctgacacca cactgtgctg gtgaggacat   1693
agctgtcatt gagaacatga agtagccctc tcttggaaga gtctgaggtg agccatagg    1753
gaagggcttc tctaggctct ttgtgactgt tgccggtagc atttaaacat tgtgcatggt   1813
gacctcaaag ggaaagcaaa tagaaaacac ccatctggtc accttacatc cagggagggt   1873
gttgtcccga ggcggcactc tgaggatgcc gtgtgctgtc cgctgagtgc tgagtgatgg   1933
acaggcagtg tctgatgcct tttgtgccca gactgtttcc cctccccctc tctcctaacg   1993
```

<210> SEQ ID NO 4
<211> LENGTH: 370
<212> TYPE: PRT
<213> ORGANISM: Unknown Organism
<220> FEATURE:
<223> OTHER INFORMATION: Description of Unknown Organism: TREK

<400> SEQUENCE: 4

```
Met Ala Ala Pro Asp Leu Leu Asp Pro Lys Ser Ala Ala Gln Asn Ser
1               5                   10                  15

Lys Pro Arg Leu Ser Phe Ser Ser Lys Pro Thr Val Leu Ala Ser Arg
            20                  25                  30

Val Glu Ser Asp Ser Ala Ile Asn Val Met Lys Trp Lys Thr Val Ser
        35                  40                  45

Thr Ile Phe Leu Val Val Val Leu Tyr Leu Ile Ile Gly Ala Ala Val
    50                  55                  60

Phe Lys Ala Leu Glu Gln Pro Gln Glu Ile Ser Gln Arg Thr Thr Ile
65                  70                  75                  80

Val Ile Gln Lys Gln Thr Phe Ile Ala Gln His Ala Cys Val Asn Ser
                85                  90                  95

Thr Glu Leu Asp Glu Leu Ile Gln Gln Ile Val Ala Ala Ile Asn Ala
            100                 105                 110

Gly Ile Ile Pro Leu Gly Asn Ser Ser Asn Gln Val Ser His Trp Asp
        115                 120                 125

Leu Gly Ser Ser Phe Phe Phe Ala Gly Thr Val Ile Thr Thr Ile Gly
    130                 135                 140

Phe Gly Asn Ile Ser Pro Arg Thr Glu Gly Gly Lys Ile Phe Cys Ile
145                 150                 155                 160

Ile Tyr Ala Leu Leu Gly Ile Pro Leu Phe Gly Phe Leu Leu Ala Gly
                165                 170                 175
```

-continued

```
Val Gly Asp Gln Leu Gly Thr Ile Phe Gly Lys Gly Ile Ala Lys Val
            180                 185                 190

Glu Asp Thr Phe Ile Lys Trp Asn Val Ser Gln Thr Lys Ile Arg Ile
        195                 200                 205

Ile Ser Thr Ile Ile Phe Ile Leu Phe Gly Cys Val Leu Phe Val Ala
210                 215                 220

Leu Pro Ala Val Ile Phe Lys His Ile Glu Gly Trp Ser Ala Leu Asp
225                 230                 235                 240

Ala Ile Tyr Phe Val Val Ile Thr Leu Thr Thr Ile Gly Phe Gly Asp
            245                 250                 255

Tyr Val Ala Gly Gly Ser Asp Ile Glu Tyr Leu Asp Phe Tyr Lys Pro
        260                 265                 270

Val Val Trp Phe Trp Ile Leu Val Gly Leu Ala Tyr Phe Ala Ala Val
    275                 280                 285

Leu Ser Met Ile Gly Asp Trp Leu Arg Val Ile Ser Lys Lys Thr Lys
290                 295                 300

Glu Glu Val Gly Glu Phe Arg Ala His Ala Ala Glu Trp Thr Ala Asn
305                 310                 315                 320

Val Thr Ala Glu Phe Lys Glu Thr Arg Arg Leu Ser Val Glu Ile
            325                 330                 335

Tyr Asp Lys Phe Gln Arg Ala Thr Ser Val Lys Arg Lys Leu Ser Ala
        340                 345                 350

Glu Leu Ala Gly Asn His Asn Gln Glu Leu Thr Pro Cys Met Arg Thr
            355                 360                 365

Cys Leu
    370

<210> SEQ ID NO 5
<211> LENGTH: 336
<212> TYPE: PRT
<213> ORGANISM: Unknown Sequence
<220> FEATURE:
<223> OTHER INFORMATION: Description of Unknown Sequence: TWIK

<400> SEQUENCE: 5

Met Leu Gln Ser Leu Ala Gly Ser Ser Cys Val Arg Leu Val Glu Arg
1               5                   10                  15

His Arg Ser Ala Trp Cys Phe Gly Phe Leu Val Leu Gly Tyr Leu Leu
            20                  25                  30

Tyr Leu Val Phe Gly Ala Val Val Phe Ser Ser Val Glu Leu Pro Tyr
        35                  40                  45

Glu Asp Leu Leu Arg Gln Glu Leu Arg Lys Leu Lys Arg Arg Phe Leu
    50                  55                  60

Glu Glu His Glu Cys Leu Ser Glu Gln Gln Leu Glu Gln Phe Leu Gly
65                  70                  75                  80

Arg Val Leu Glu Ala Ser Asn Tyr Gly Val Ser Val Leu Ser Asn Ala
                85                  90                  95

Ser Gly Asn Trp Asn Trp Asp Phe Thr Ser Ala Leu Phe Phe Ala Ser
            100                 105                 110

Thr Val Leu Ser Thr Thr Gly Tyr Gly His Thr Val Pro Leu Ser Asp
        115                 120                 125

Gly Gly Lys Ala Phe Cys Ile Ile Tyr Ser Val Ile Gly Ile Pro Phe
    130                 135                 140

Thr Leu Leu Phe Leu Thr Ala Val Val Gln Arg Ile Thr Val His Val
145                 150                 155                 160
```

```
Thr Arg Arg Pro Val Leu Tyr Phe His Ile Arg Trp Gly Phe Ser Lys
                165                 170                 175

Gln Val Val Ala Ile Val His Ala Val Leu Leu Gly Phe Val Thr Val
            180                 185                 190

Ser Cys Phe Phe Phe Ile Pro Ala Ala Val Phe Ser Val Leu Glu Asp
        195                 200                 205

Asp Trp Asn Phe Leu Glu Ser Phe Tyr Phe Cys Phe Ile Ser Leu Ser
    210                 215                 220

Thr Ile Gly Leu Gly Asp Tyr Val Pro Gly Glu Gly Tyr Asn Gln Lys
225                 230                 235                 240

Phe Arg Glu Leu Tyr Lys Ile Gly Ile Thr Cys Tyr Leu Leu Leu Gly
                245                 250                 255

Leu Ile Ala Met Leu Val Val Leu Glu Thr Phe Cys Glu Leu His Glu
            260                 265                 270

Leu Lys Lys Phe Arg Lys Met Phe Tyr Val Lys Lys Asp Lys Asp Glu
        275                 280                 285

Asp Gln Val His Ile Ile Glu His Asp Gln Leu Ser Phe Ser Ser Ile
    290                 295                 300

Thr Asp Gln Ala Ala Gly Met Lys Glu Asp Gln Lys Asn Glu Pro
305                 310                 315                 320

Phe Val Ala Thr Gln Ser Ser Ala Cys Val Asp Gly Pro Ala Asn His
325                 330                 335

<210> SEQ ID NO 6
<211> LENGTH: 394
<212> TYPE: PRT
<213> ORGANISM: Unknown Sequence
<220> FEATURE:
<223> OTHER INFORMATION: Description of Unknown Sequence: TASK

<400> SEQUENCE: 6

Met Lys Arg Gln Asn Val Arg Thr Leu Ala Leu Ile Val Cys Thr Phe
  1               5                  10                  15

Thr Tyr Leu Leu Val Gly Ala Ala Val Phe Asp Ala Leu Glu Ser Glu
             20                  25                  30

Pro Glu Leu Ile Glu Arg Gln Arg Leu Glu Leu Arg Gln Gln Glu Leu
         35                  40                  45

Arg Ala Arg Tyr Asn Leu Ser Gln Gly Gly Tyr Glu Glu Leu Glu Arg
     50                  55                  60

Val Val Leu Arg Leu Lys Pro His Lys Ala Gly Val Gln Trp Arg Phe
 65                  70                  75                  80

Ala Gly Ser Phe Tyr Phe Ala Ile Thr Val Ile Thr Thr Ile Gly Tyr
                 85                  90                  95

Gly His Ala Ala Pro Ser Thr Asp Gly Gly Lys Val Phe Cys Met Phe
            100                 105                 110

Tyr Ala Leu Leu Gly Ile Pro Leu Thr Leu Val Met Phe Gln Ser Leu
        115                 120                 125

Gly Glu Arg Ile Asn Thr Leu Val Arg Tyr Leu Leu His Arg Ala Lys
    130                 135                 140

Lys Gly Leu Gly Met Arg Arg Ala Asp Val Ser Met Ala Asn Met Val
145                 150                 155                 160

Leu Ile Gly Phe Phe Ser Cys Ile Ser Thr Leu Cys Ile Gly Ala Ala
                165                 170                 175

Ala Phe Ser His Tyr Glu His Trp Thr Phe Phe Gln Ala Tyr Tyr Tyr
            180                 185                 190
```

```
Cys Phe Ile Thr Leu Thr Thr Ile Gly Phe Gly Asp Tyr Val Ala Leu
        195             200             205

Gln Lys Asp Gln Ala Leu Gln Thr Gln Pro Gln Tyr Val Ala Phe Ser
        210             215             220

Phe Val Tyr Ile Leu Thr Gly Leu Thr Val Ile Gly Ala Phe Leu Asn
225             230             235                         240

Leu Val Val Leu Arg Phe Met Thr Met Asn Ala Glu Asp Glu Lys Arg
                245             250             255

Asp Ala Glu His Arg Ala Leu Leu Thr Arg Asn Gly Gln Ala Gly Gly
            260             265             270

Gly Gly Gly Gly Gly Ser Ala His Thr Thr Asp Thr Ala Ser Ser Thr
        275             280             285

Ala Ala Ala Gly Gly Gly Gly Phe Arg Asn Val Tyr Ala Glu Val Leu
        290             295             300

His Phe Gln Ser Met Cys Ser Cys Leu Trp Tyr Lys Ser Arg Glu Lys
305             310             315             320

Leu Gln Tyr Ser Ile Pro Met Ile Ile Pro Arg Asp Leu Ser Thr Ser
                325             330             335

Asp Thr Cys Val Glu Gln Ser His Ser Ser Pro Gly Gly Gly Gly Arg
            340             345             350

Tyr Ser Asp Thr Pro Ser Arg Arg Cys Leu Cys Ser Gly Ala Pro Arg
            355             360             365

Ser Ala Ile Ser Ser Val Ser Thr Gly Leu His Ser Leu Ser Thr Phe
        370             375             380

Arg Gly Leu Met Lys Arg Arg Ser Ser Val
385             390
```

MECHANOSENSITIVE MAMMALIAN POTASSIUM CHANNEL ACTIVATABLE BY POLYUNSATURATED FATTY ACIDS

RELATED APPLICATION

This application is a application Ser. No. 09/655,272, filed Sep. 5, 2000, now U.S. Pat. No. 6,942,979, which is a continuation of International Application No. PCT/FR99/00404, with an international filing date of Feb. 23, 1999, which is based on French Patent Application No. 98/02725, filed Mar. 5, 1998.

TECHNICAL FIELD

This disclosure concerns a new class of mechanosensitive potassium channels activated by polyunsaturated fatty acids. The disclosure is based on the discovery of a new mechanosensitive potassium channel, sometimes hereinafter referred to as "TRAAK" as an abbreviation for TWIK-Related AA-ACTIVATED $K^+$ channel, which is activated by polyunsaturated fatty acids as well as by the neuroprotective agent riluzole. The properties of the channels of the TRAAK family as well as their tissue distribution give these channels a primordial role in the transport of potassium in a large number of cell types.

BACKGROUND

Potassium channels are ubiquitous proteins and their exceptional functional diversity makes them ideal candidates for a large number of biological processes. They intervene notably in the regulation of neuronal and muscular excitability, cardiac rhythm and hormone secretion. Three structural types of potassium channels have been described in mammals. The first is the Shaker type which is composed of subunits that have six transmembranal segments and one P domain which is implicated in the formation of the ionic pore. The second is the IRK type which has two transmembranal segments and one P domain. The third has been described more recently and corresponds to the TWIK type which has four transmembranal segments and two P domains. Three channels of this type have been identified: TWIK-1 (Fink, M. et al. EMBO J. 15, 6854-6862 [1996]; Lesage, F. et al. EMBO J. 15, 1004-1011 [1996]), TREK-1 and TASK (Duprat, F. et al. EMBO J. 16, 5464-5471 [1997]). In addition to a conserved general structure, they have primary sequences exhibiting little similarity since they present between 20 and 25% amino acid identity.

SUMMARY

We accordingly provide, among other things, a purified protein, antibodies, nucleic acids, vectors and various methods as follows:

a purified protein comprising a mechanosensitive potassium channel activated by at least one polyunsaturated fatty acid and riluzole;

a purified nucleic acid molecule comprising a nucleic acid sequence encoding the protein;

a vector comprising the purified nucleic acid molecule operably linked to regulatory sequences;

a method for producing the purified protein comprising:
a) transferring the nucleic acid molecule into a cellular host;
b) culturing said host under suitable conditions to produce a protein comprising a potassium channel; and
c) isolating the protein of step (b);

a method for expressing the potassium channel comprising:
a) transferring the purified nucleic acid molecule into a cellular host; and
b) culturing said host under suitable conditions for expressing the potassium channel;

a cellular host produced by the method;

a method for screening substances capable of modulating the activity of the purified protein comprising:
a) reacting varying amounts of the substance to be screened with the cellular host; and
b) measuring the effect of the substance to be screened on a potassium channel expressed by the cellular host;

a method for preventing or treating heart disease in mammals which comprises administering a therapeutically effective amount of a pharmaceutical composition comprising a therapeutically effective amount of a substance capable of modulating the activity of the purified protein;

a method for preventing or treating central nervous system disease in mammals which comprises administering a therapeutically effective amount of a pharmaceutical composition comprising a therapeutically effective amount of a substance capable of modulating the activity of the purified protein; and a pharmaceutical composition comprising a therapeutically effective amount of the purified protein and a pharmaceutically acceptable carrier.

BRIEF DESCRIPTION OF THE DRAWINGS

Other advantages and characteristics will become apparent upon reading the text and examples below which explain the identification and characterization of these mechanosensitive potassium channels which are activated by fatty acids. These examples will refer to the attached sequences and drawings in which:

FIG. 1, which contains SEQ ID No: 1, represents the nucleotide sequence of the cDNA of TRAAK and the amino acid sequence (SEQ ID No: 2) of the coding sequence.

FIG. 2 represents alignment of the sequences of TWIK-1, (SEQ ID No: 5), TREK-1 (SEQ ID No: 4), TASK (SEQ ID No: 6) and TRAAK (SEQ ID No: 2), which are four channels of the TWIK type presently cloned in mammals as well as the deduced dendrogram of this alignment.

FIG. 4 shows the electrophysiological properties of the TRAAK currents recorded using the imposed voltage technique on Xenopus oocytes that had received an injection of TRAAK cRNA (a, b, c) and on COS cells transfected with a vector expressing TRAAK (d, e).

FIGS. 5a and b are graphs showing the effect of the osmolarity of the external medium on oocytes that received an injection of TREK-1 or TASK cRNA.

FIGS. 6a-h are graphs showing that TREK-1 is a mechanosensitive potassium channel in the transfected COS cells.

FIGS. 8a-f are graphs showing the activation of TREK-1 by arachidonic acid in the transfected COS cells.

FIGS. 9a-e are graphs showing the effect of arachidonic acid and other fatty acids on the TRAAK channel expressed in the transfected COS cells.

FIGS. 10a and b are graphs showing the effect of riluzole on the TREK-1 and TRAAK designated TREK-2 currents.

DETAILED DESCRIPTION

Figure 3:
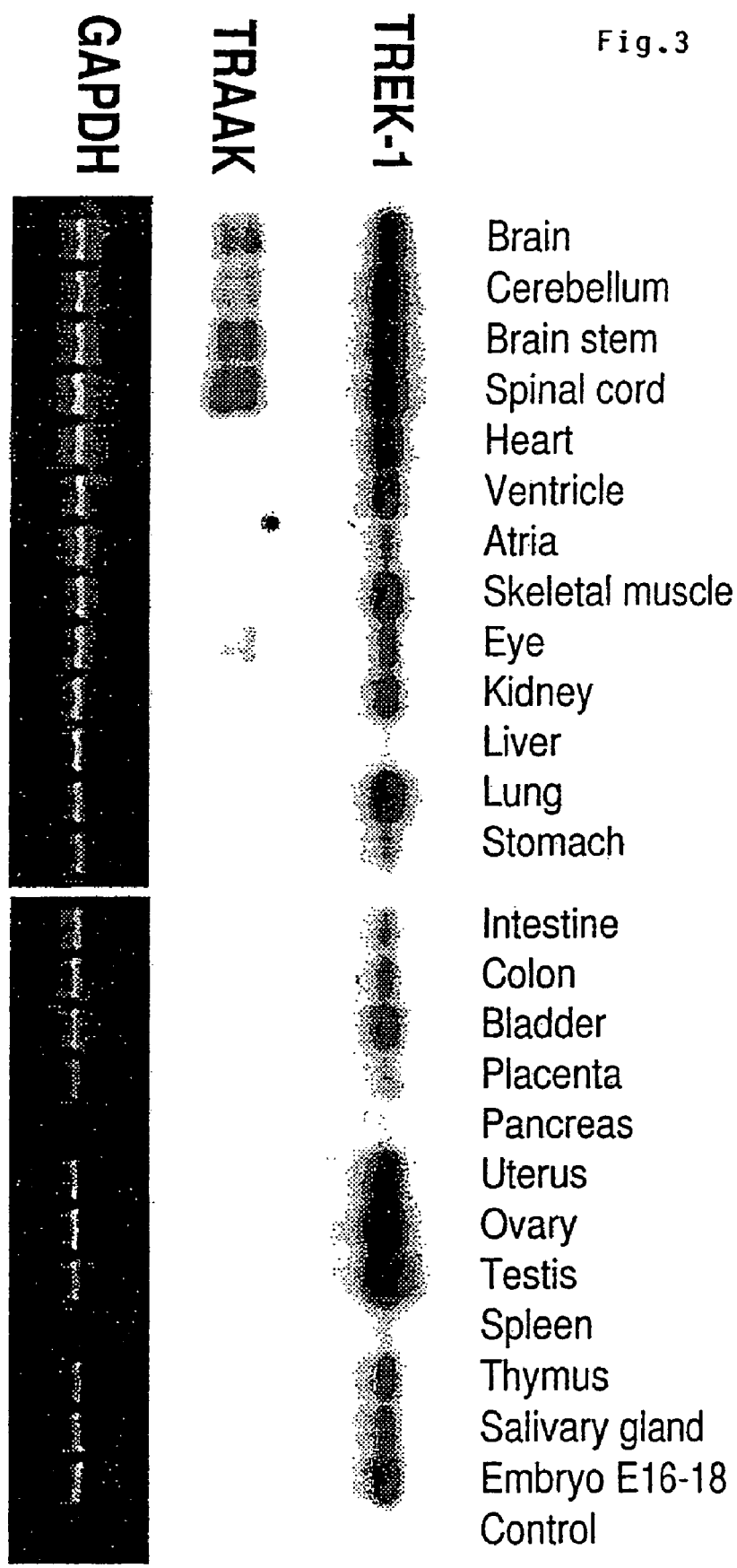
FIG. 3 represents the RT-PCR analysis of the distribution of TREK-1 and TRAAK in the tissues of the adult mouse.

We discovered and cloned a new channel designated TRAAK, which is a member of the TWIK channel family. The gene coding this channel is most particularly homologous at the level of its amino acid sequence with the TREK-1 channel with which it exhibits 38% amino acid identity. The disclosure is also based on the unique electrophysiological properties of the TREK-1 and TRAAK channels. In fact, both of these channels produce potassium-selective currents which are activated by a tension applied to the cell membrane, which channels are referred to as mechanosensitive, or by the application of polyunsaturated fatty acids, especially arachidonic acid which is an essential messenger of intercellular and intracellular communication and an important modulator of neuronal excitability (Ordway, R. W., Singer, J. J. and Walsh, J. V. 14, 96-100 [1991]; Bliss, T. V. P. and Collingridge, G. L. Nature 31-39 [1993]; Piomelli, D. Curr. Opin. Cell. Biol. 5, 274-280 [1993]; Meves, H. Prog. Neurobiol. 43, 175-186 [1994]; Piomelli, D. Crit. Rev. Neurobiol. 8,65-83 [1994]. These channels are also opened by riluzole which is a neuroprotective agent (Malgouris, C. et al. J. Neurosci. 9, 3720-3727 [1989]; Pratt, J. et al. Neuroscience. Lett. 140, 225-230 [1992]) used clinically to prolong the lives of patients with amyotrophic lateral sclerosis.

The discovery of this new class of potassium channels and the heterologous expression of these channels provides us notably with new research tools for screening drugs that are capable of modulating the activity of the potassium channels and thus of preventing or treating diseases implicating these channels such as epilepsy, cardiac pathologies (arrhythmias) and vascular diseases, neurodegenerative diseases, especially those associated with ischemia and anoxia, the endocrine diseases associated with defective hormone secretion and muscle diseases.

Thus, we a purified protein constituting a mechanosensitive potassium channel activated by polyunsaturated fatty acids, especially arachidonic acid, and by riluzole. More specifically, we provide a protein constituting the TRAAK channel, the amino acid sequence of which is represented in the attached sequence list as SEQ ID No: 2 or a functionally equivalent derivative of this protein.

Such derivatives include those with a sequence comprising a modification and/or a suppression and/or an addition of one or more amino acid residues, as long as this modification and/or suppression and/or addition does not modify the properties of the TRAAK channel. Such derivatives can be analyzed by the expert in the field using the techniques described in the examples presented below which enable demonstration of the biophysical and pharmacological properties of the TRAAK channel. More specifically, such a derivative is the TREK-1 channel the amino acid sequence of which is represented in the attached sequence list as SEQ ID No: 4.

Polyclonal or monoclonal antibodies directed against at least one protein constituting an ionic channel according to the invention can be prepared by the classic methods described in the literature. These antibodies are useful for detecting the presence of the ionic channels of the invention in various human and animal tissues; however, because of their specificity, they can also find therapeutic applications for the in vivo inhibition or activation of a TRAAK channel and/or its derivatives.

We also provide a purified nucleic acid molecule comprising or constituted by a nucleic sequence coding for a protein constituting a mechanosensitive potassium channel activated by polyunsaturated fatty acids, especially arachidonic acid, and by riluzole. More specifically, we provide a nucleic acid molecule comprising at least one sequence coding for the protein constituting the TRAAK channel, the amino acid sequence of which is represented in the attached sequence list as SEQ ID No: 2 or for a functionally equivalent derivative of this protein. A DNA molecule comprising the sequence coding for the TRAAK protein is represented in the attached sequence list as SEQ ID No: 1 or its complementary sequence. More specifically, such a nucleic acid sequence comprises the sequence between nucleotides 284 and 1477 of SEQ ID No: 1 or its complementary sequence.

Another nucleic acid sequence comprises at least one sequence coding for the protein constituting the TREK-1 channel which has the amino acid sequence represented in the attached sequence list as SEQ ID No: 4 or for a functionally equivalent derivative of this protein. A DNA molecule comprising the sequence coding for the TREK-1 protein is represented in the attached sequence list as SEQ ID No: 3 or its complementary sequence. More specifically, such amino acid sequence comprises the sequence between nucleotides 484 and 1596 of SEQ ID No: 3.

We also provide a vector comprising at least one of the preceding nucleic acid molecules, advantageously associated with suitable control sequences, as well as a process for the production or expression in a cellular host of a protein constituting an ionic channel according to the invention. The preparation of these vectors as well as the production or expression in a host of the channels of the invention can be implemented by molecular biology and genetic engineering techniques which are well known to the expert in the field.

As an example, a process for the production of a protein constituting a cationic channel according to the invention comprises:
  transferring a nucleic acid molecule or a vector containing said molecule into a cellular host,
  culturing said cellular host under conditions enabling production of the protein constituting the potassium channel,
  isolating by any suitable means the proteins constituting the potassium channels of the invention.

As an example, a process for the expression of an ionic channel according to the invention comprises:
  transferring a nucleic acid molecule of the invention or a vector containing said molecule into a cellular host,
  culturing said cellular host under conditions enabling expression of the potassium channels.

The cellular host employed in the preceding processes can be selected from among the prokaryotes or the eukaryotes and especially from among the bacteria, yeasts, and mammal, plant or insect cells.

The vector employed is selected on the basis of the host into which it will be transferred; all vectors such as plasmids can be employed.

Thus, the disclosure also pertains to the cellular hosts and more specifically the transformed cells expressing the potassium channels exhibiting the properties and structure of the type of TRAAK channel cells obtained in accordance with the preceding processes. These cells are useful for screening substances capable of modulating the TRAAK channel currents. This screening is implemented by bringing into contact variable quantities of a substance to be tested with cells expressing the channels of the invention, then measuring by any suitable means the possible effects of said substance on the potassium currents of said channels. Electrophysiological techniques also make these studies possible and are also the object of the present invention when employed with TRAAK channels or their derivatives. This screening process makes it possible to identify drugs that can modulate the activity of the potassium channels and thus might be able to prevent or treat the diseases in which these channels are implicated. These substances and their use as drugs, isolated and detected by means of the above process, are also part of the invention.

More specifically, we provide a chemical or biological substance capable of modifying the currents of a potassium channel according to the invention for the preparation of a drug that is useful in the prevention or treatment of diseases of the heart or nervous system in human or animal subjects, such as cardiac pathologies (arrhythmias) and vascular diseases, neurodegenerative diseases, especially those associated with ischemia and anoxia, endocrine diseases associated with defective hormone secretion and muscle diseases.

A nucleic acid molecule coding for a protein constituting a TRAAK channel or a derivative thereof, or a vector comprising this nucleic acid molecule or a cell expressing TRAAK channels are also useful for the preparation of transgenic animals. These can be animals that over express said channels, but more especially knock-out animals, e.g., animals presenting a deficiency in these channels; these transgenic animals are prepared by methods which are known to the expert in the field, and allow preparation of live models for studying the animal pathologies associated with the TRAAK channels.

These transgenic animals as well as the previously described cellular hosts are useful as models for studying the pathologies associated with these mechanosensitive potassium channels which are activated by polyunsaturated fatty acids either because they over express the potassium channels of the TRAAK channel type or because they present a deficiency in these potassium channels.

In addition, a protein constituting a neuronal ionic TRAAK channel can also be useful for the manufacture of drugs intended to treat or prevent the diseases in which these channels are implicated. The disclosure thus also pertains to the pharmaceutical compositions comprising as active principle at least one of these proteins possibly combined with a physiologically acceptable vehicle.

In fact, the nucleic acid molecules or the cells transformed by the molecules are suitable for use in gene therapy strategies to compensate for a TRAAK channel deficiency at the level of one or more tissues of a patient. The disclosure thus also pertains to a drug comprising the nucleic acid molecules of the invention or cells transformed by the molecules for the treatment of diseases in which the TRAAK channels or their derivatives are implicated.

FIG. 1, which contains SEQ ID No: 1, represents the nucleotide sequence of the cDNA of TRAAK and the corresponding amino acid sequence SEQ ID No: 2.

FIG. 2 represents alignment of the sequences of TWIK-1 (SEQ ID No: 5), TREK-1(SEQ ID No: 4), TASK (SEQ ID No: 6), and TRAAK (SEQ ID No: 2), which are four channels of the TWIK type presently cloned in mammals as well as the deduced dendrogram of this alignment. Identical residues are represented on a black background and the conserved residues are represented on a gray background.

FIG. 3 represents the RT-PCR analysis of the distribution of TREK-1 and TRAAK in the tissues of the adult mouse. Fragments of the transcripts coding for TREK-1 and TRAAK were amplified by PCR using specific oligonucleotides, transferred onto a nylon membrane then labeled with oligonucleotides internally marked with phosphorus 32.

FIG. 4 shows the electrophysiological, properties of the TRAAK currents recorded using the imposed voltage technique on Xenopus oocytes that had received an injection of TRAAK cRNA (a, b, c) and on COS cells transfected with a vector expressing TRAAK (d, e, f). In (a): the oocytes were maintained at a potential of −80 mV then the currents were recorded following potential jumps from −150 to +50 mV by increments of 20 mV. The recordings were performed in an external medium containing a $K^+$ concentration of 2 mM or 74 mM. In (b): current-potential relation was according to the same experimental set-up as in (a). In (c): potential reversal (Erev) of the TRAAK currents were a function of the external $K^+$ concentration. In (d): currents recorded on COS cells transfected by TRAAK according to the same protocol as in (a). In (e): current-potential relation was according to the same experimental set-up as in (d).

FIG. 5 shows the effect of the osmolarity of the external medium on oocytes that received an injection of TREK-1 or TASK cRNA. In FIG. 5*a*: comparison of the effects of the application of a hypertonic solution (417 mOsm, by addition of mannitol) on control oocytes (CD8) and on oocytes expressing TASK or TREK-1 are shown. The currents were measured after a potential jump from −80 to +80 mV. The inset shows the TREK-1 current before and after (indicated by an arrow) the application of the hypertonic solution. In FIG. 5*b*: reversible effect of a hypertonic solution (434 mOsm, by addition of sucrose) on the current-potential relations deduced from the potential ramps which lasted 600 msec is shown. The inset shows the kinetics of the effect produced by the hypertonic solution. The currents were measured at 80 mV.

FIG. 6 shows that TREK-1 is a mechanosensitive potassium channel in the transfected COS cells. In FIG. 6*a*: channel activities (N*Po) in the membrane patches were maintained at 0 mV and obtained in the attached cell configuration from control cells (CD8) or from cells transfected by TREK-1 and TASK. In FIG. 6*b*: stretching the membrane had no effect on the activity of the TASK channel (attached cell configuration). The patch was maintained at 50 mV. In FIG. 6*c*: the TREK-1 channels were silent at rest and opened upon tension of the membrane. The patch was maintained at +50 mV. In FIG. 6*d*: the histogram shows the amplitude of the channel activity generated by the membrane tension and illustrated in FIG. 6*f*. In FIG. 6*e*: current-potential relation in a single TREK-1 channel (n=6) is seen. The conductance of 81 pS, was calculated between 0 and 80 mV. In FIG. 6*f*: activation of TREK-1 by stretching the membrane (30 mmHg) in the inside-out configuration is shown. The maintenance potential was 100 mV. In FIG. 6*g*: effects produced by higher and higher tensions (5 seconds duration) on the current-potential relation of a patch expressing TREK-1 are shown. In FIG. 6*h*: dose-effect curve of the activation of TREK-1 by the tension (n=6) is seen. The curve was traced by following the experimental points according to the Boltzmann relation.

Figure 7:
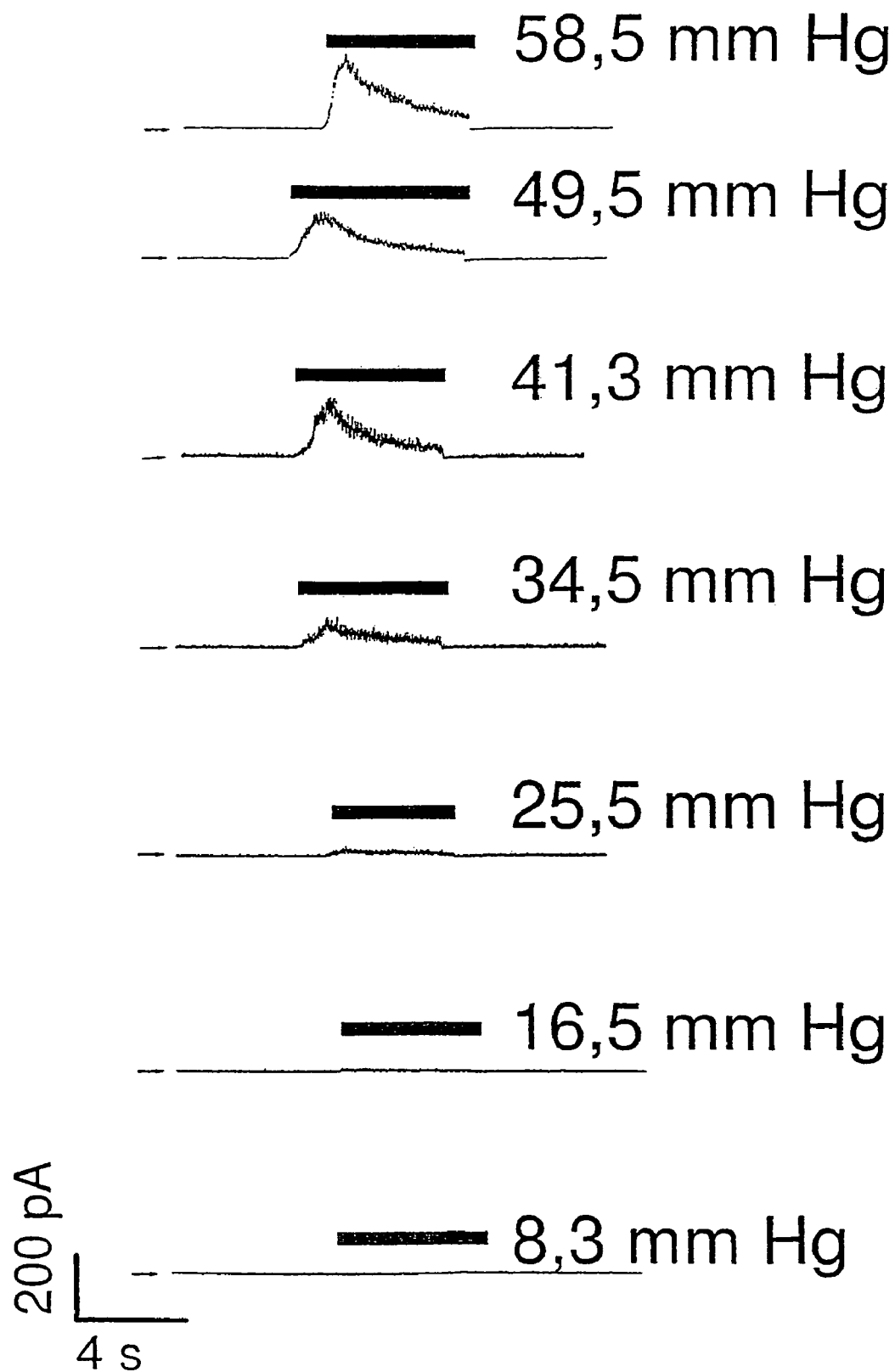
FIG. 7 shows the activation of TRAAK by stretching the cellular membrane in the transfected COS cells.

FIG. 7 shows the activation of TRAAK by stretching the cellular membrane in the transfected COS cells. The current was recorded at 0 mV in the inside-out configuration. The depressions applied via the recording pipette are indicated to the right of the tracings.

FIG. 8 shows the activation of TREK-1 by arachidonic acid in the transfected COS cells. In FIG. 8*a*: the activity of TREK-1 was recorded in the attached cell configuration. The patch was stimulated by a potential ramp lasting 800 msec every 5 seconds. The currents were measured at 80 mV. The applications of arachidonic acid (AA, 10 µM) are indicated by the horizontal bars. During the experiment, the patch was stimulated by tensions of 50 mmHg (indicated by the arrows). At 9 minutes, the patch was excised in the inside-out configuration. In FIG. 8*b*: current-potential relations corresponding to the experiment illustrated in FIG. 8*a* is shown. In FIG. 8*c*: activity of TREK-1 in the attached cell configuration with 10 µM AA in the pipette can be seen. The potential ramp lasted 800 msec and the currents were measured at 80 mV. In FIG. 8*d*: single-channel current-potential relations at the moment at which the pipette was placed on the membrane or after 20 minutes and 1 minute after the patch was excised in the inside-out configuration. In FIG. 8*e*: effect of AA (10 µM) on the TREK-1 current recorded in the intact cell is demonstrated. The current was measured at 80 mV. In FIG. 8*f*: AA had no effect on the TREK-1 current measured in the intact cell when it was in the pipette. The current was measured 30 minutes after the patch was broken (control tracing) by a potential ramp of 800 msec. The current was then measured after an application of AA of 1 minute in the external medium (AA tracing).

FIG. 9 shows the effect of arachidonic acid and other fatty acids on the TRAAK channel expressed in the transfected COS cells. In FIG. 9*a*: current-potential relations obtained from potential ramps of 5 W msec from −150 to +50 mV, after application of AA (10 µM) and after washing are shown. The inset shows the currents triggered by the potential jumps from −130 to +50 mV in increments of 20 mV. The maintenance potential was −80 mV. In FIG. 9*b*: dose-effect relation of the activation of TRAAK by AA is shown. In FIG. 9*c*: current-potential relations obtained as in FIG. 9*a* in the outside-out configuration are shown. The inset shows the effect of AA at 20 mV. In FIG. 9*d*: a histogram represents the coefficient of augmentation of the currents obtained after application of various fatty acids (10 µM). In FIG. 9*e*: the histogram shows the value of the currents recorded in the intact cell configuration before and after application of AA on the cells temporarily transfected by TWIK-1, TASK, TREK-1 and TRAAK and on the cells transfected in a stable manner by TRAAK. The coefficient of augmentation is indicated in each case.

FIGS. 10*a* and *b* are graphs showing the effect of riluzole on the TREK-1 and TRAAK designated TREK-2 currents. The current-potential relations were obtained as in FIG. 9*a* above and after application of riluzole (100 µM) on the transfected COS cells. The inset shows the effects of riluzole on the currents recorded in the outside-out configuration.

I. Cloning, primary structure and tissue distribution of TRAAK The sequence of the TWIK-1 channel was used to detect homologous sequences in public DNA data libraries (Genbank and EMBL) employing the BLAST alignment program. It was thereby possible to identify a human TAG expressed sequence which was used to screen a library of mouse brain cDNA. Multiple clones were isolated and characterized. The longest was sequenced. The following characteristics were determined:

The isolated cDNA contained an open reading phase of 1197 nucleotides coding for a polypeptide of 398 residues. The nucleotide and protein sequences are shown in FIG. 1.

This protein contains four potential transmembranal segments and two P domains. It thus has the same general structure as the TWIK-1, TREK-1 and TASK channels. In addition, it exhibits sequence homologies with these channels: about 20-25% identity with TWIK-1 and TASK and about 38% identity with TREK-1. With the exception of the P domains which are present in all of the cloned potassium channels, it has no significant sequence homology with the channels of the Shaker and IRK type. It, therefore, belongs to the TWIK-1 family and its closest homologue is TREK-1. These relations can be seen in FIG. 2 at the level of the alignment of the protein sequences as well as in the dendrogram which was deduced from this alignment. TRAAK and TREK-1 thus form a structural subclass within the TWIK-1 family.

The sequences of various oligonucleotides were deduced from the sequence of TRAAK. These oligonucleotides enabled the use of RT-PCR to study the distribution of the transcript coding for TRAAK in adult mouse tissues. As shown in FIG. 3, TRAAK is exclusively expressed in the neural tissues: brain, cerebellum, spinal cord and retina. This distribution is very different from that of its closest homologue which is the TREK-1 channel. This substance has an almost ubiquitous distribution and is present in the excitatory tissues as well as the nonexcitatory tissues.

II. Functional expression of TRAAK

For the functional study, the coding sequence of TRAAK was inserted in the vector pEXO and a complementary RNA (cRNA) was synthesized from this construction and injected in Xenopus oocytes. For expression in the COS cells, the TRAAK sequence was subcloned in an expression vector under the control of a eukaryote promoter and transfected into the cells. An absent non-inactivating current from the oocytes and the control cells was measured by the imposed voltage technique as represented in FIG. 4. The activation was instantaneous and could not be resolved because it was masked by the capacitive discharge of the current recorded at the beginning of the potential jump. The current-potential relation rectified in the outgoing direction when the external $K^+$ concentration was equal to 2 mM. Incoming currents were observed when the external $K^+$ concentration was increased. At all concentrations, the current-potential curves followed the Goldman-Hodgkin-Katz relation. This demonstrates that the TRAAK currents have no rectification other than that which is due to the dyssymmetrical concentrations of $K^+$ on each side of the membrane and that TRAAK is a channel which is not potential-dependent. The TRAAK channel is selective for potassium. Reversal of the current potential follows the equilibrium potential of K+ and changing the concentration of $K^+$ by 10 leads to a change in the potential inversion value conforming to the value predicted by Nernst's equation (48.7±0.7 mV times 10, n=4).

The properties of TRAAK, absence of activation and inactivation kinetics as well as its opening at all membrane potentials, are the characteristics of the potassium channels known as leakage channels. As to be expected for channels of this type, their expression in oocytes is associated with a strong polarization. The resting potential of the membrane passes from −43±2.4 m V (n=7) in the control oocytes to −88±1.4 mV (n=23) in the transfected oocytes, a value close to the equilibrium potential of potassium. TRAAK was also expressed in the transfected COS-M6 cells. In this system as well, the TRAAK currents were instantaneous and were not inactivated. The recording of the patch in outside-out configuration indicated a unit conductance of TRAAK equal to 45.5±3.7 pS (n 10).

III. TREK-1 and TRAAK are mechanosensitive channels

It has been established that the structural subclass formed by the TREK-1 and TRAAK $K^+$ channels are associated with electrophysiological properties which are unique among the TWIK type $K^+$ channels. The TREK-1 and TRAAK channels are, in fact, activated by a tension applied to the plasma membrane. This tension is obtained either indirectly by changing the osmolarity of the external medium and thus the volume of the cell or more directly by applying a depression in the recording pipette. The following characteristics were demonstrated:

FIG. 5 demonstrates that the expression of the TREK-1 channel in the Xenopus oocytes, which were maintained in a hypotonic medium, induced instantaneous, non-inactivating currents. When the osmolarity of the external medium was increased by adding mannitol to it, a noteworthy decrease in the amplitude of the current of TREK-1 was seen which demonstrates a sensitivity of the channel to the cell volume. In contrast, the TASK channel is not affected by the osmolarity of the external medium.

FIG. 6 demonstrates that the TREK-1 channel is mechanosensitive. In the transfected COS cells and under resting conditions, the activity of TREK-1 was undetectable in the attached cell configuration whereas the activity of TASK was easily measurable under the same conditions. However, a depression applied to the membrane by means of the recording pipette triggered an opening of the TREK-1 channel. No such effect was seen with TASK. The activation of TREK-1 induced by the tension was also obtained in the inside-out configuration, i.e., when the patch was excised and the internal surface of the membrane was in contact with the external medium. In this configuration, the activity of the channel was also absent or very weak if tension was not applied to the membrane. The effect of the tension was gradual and an activation equal to half of the maximum value was detected for a depression equivalent to 23 mmHg. In addition, FIG. 6h shows that the activation induced by stretching is independent of the membrane potential.

FIG. 7 also shows that TRAAK is a channel activated by stretching. In the absence of depression or for low values, the TRAAK channel was inactive. For higher values, the channel was activated and a current was recorded. During the application of the depression, a decrease in the activity of the channel could be seen as was the case with TREK-1.

IV. TREK-1 and TRAAK are activated by arachidonic acid and other polyunsaturated fatty acids.

Activation of the TREK-1 and TRAAK channels by mechanical stretching of the membrane is mimicked by the application of arachidonic acid and by the application of other polyunsaturated fatty acids but not by the application of saturated fatty acids. The following characteristics were demonstrated:

FIG. 8 demonstrates that TREK-1 is activated by arachidonic acid (AA). The application of AA on the control cells (CD8) had no effect. The activations obtained by stretching of the membrane and by application of AA are similar in amplitude but are not additive. The two types of activation were suppressed in the attached cell configuration. When the recording pipette contained AA, excision of the patch in the inside-out configuration induced in a reproducible manner a noteworthy increase in the activity of TREK-1. Similarly, the amplitude of the activation induced by a depression applied in the recording pipette was greater when the patch was excised. Finally, it was seen that in the intact cell, internal AA did not activate TREK-1. When the cell was dialyzed for periods as long as 30 minutes, no channel activation from the internal AA took place even though activation could be seen just a few seconds after the application of AA in the external medium. These results indicate that AA activates TREK-1 solely when it is applied on the external surface of the membrane.

FIG. 9 demonstrates that the TRAAK channel is activated by AA in the same manner as TREK-1. The activation was reversible and dependent on the concentration applied. This activation was also seen in the outside-out configuration. Activation of TRAAK by AA was not prevented when the AA perfusion contained a mixture of inhibitors of AA metabolism (norhydroguaiaretic acid for lipoxygenase, indomethacin for cyclooxygenase, clotrimazole for epoxygenase and ETYA which inhibits all of the metabolism pathways of AA, all at 10 mM). Under these conditions, the increase in the current induced by AA was 6.6±0.5 times (n=3) (at +50 mV). An increase of 1.7±0.4 times (n=3) in the background potassium current could be seen after administration of a cocktail of inhibitors in the absence of AA. This result demonstrates that the activation by AA does not require the transformation of the AA into eicosanoids.

FIG. 9 also demonstrates that fatty acids other than AA activate the channel. This activation is specific to the polyunsaturated cis fatty adds and was seen with oleic (C18Δ9), linoleic add (C18Δ9,12), linolenic (C18Δ9, 12, 15), eicosapentaenoic (EPA, C2OΔ5, 8, 11, 14, 17) and docosohexaenoic (DORA, C2OΔ4,7,10,13,16,19) acids at a concentration of 10 mM. The saturated acids such as palmitic (C16), stearic (C18) and arachidic (C20) acids had no effect. The derivatives of AA and docosohexaenoic acid in which the carboxylic group is substituted by an alcohol group (AA-OH) or the methyl esters (AA-ME, DOHA-ME) are also inactive against TRAAK. The effect of AA on TRAAK can be seen on the cells that were transfected in a temporary manner as well as those transfected in a stable manner (three independent stable cell lines were tested).

Finally, FIG. 9 demonstrates that the effect of activation by AA is specific to TREK-1 and TRAAK. No effects of the same type were seen for the TWIK-1 and TASK channels.

In the oocytes, TRAAK was insensitive to the classic potassium channel blocking agents such as tetraethylammonium (TEA, 1 mM), 4-aminopyridine (4-AP, 1 mM) and quinine (100 mM). In contrast, $Ba^{2+}$, (1 mM) blocked 56.7±4.6%, n=5, of the TRAAK current at +40 mV.

V. The TREK-1 and TRAAK channels are activated by riluzole, a neuroprotective agent Riluzole is a neuroprotective agent used to prolong the survival of patients with amyotrophic lateral sclerosis. FIG. 10 demonstrates that this pharmacological agent is an opener of the TREK-1 and TRAAK channels. TREK-1 and TRAAK are the first ionic channels to exhibit activity stimulated by riluzole.

What is claimed is:

1. A purified protein comprising a mechanosensitive potassium channel comprising four transmembranal segments and two P domains activated by at least one polyunsaturated fatty acid and riluzole where the purified protein is selected from the group consisting of a purified protein encoded by the nucleic acid sequence of SEQ ID NO: 1, a purified protein comprising the amino acid sequence of SEQ ID NO: 2, and a purified protein comprising an amino acid sequence having at least 95% identity to the amino acid sequence of SEQ ID NO: 2.

2. The purified protein of claim 1, wherein the polyunsaturated fatty acid is arachidonic acid.

3. A composition comprising an effective amount of at least one purified protein of claim 1 or claim 2 and an acceptable carrier.

4. An isolated peptide chain comprising an amino acid sequence having at least 95% identity to the amino acid sequence shown in SEQ ID NO: 2.

5. The isolated peptide chain of claim 4 comprising the amino acid sequence shown in SEQ ID) NO: 2.

6. The isolated peptide chain of claim 4 comprising amino acid residues 2 to 398 shown in SEQ ID NO: 2.

7. A composition comprising an effective amount of at least one isolated peptide chain of claim 4, 5, or 6 and an acceptable carrier.

* * * * *